United States Patent
Ostrom

(10) Patent No.: US 6,864,230 B2
(45) Date of Patent: Mar. 8, 2005

(54) GLUTAMINE RICH DIETARY COMPOSITION

(75) Inventor: Steven M. Ostrom, Minnetonka, MN (US)

(73) Assignee: Novartis Nutrition AG, Berne (CH)

( * ) Notice: Subject to any disclaimer, the term of this patent is extended or adjusted under 35 U.S.C. 154(b) by 88 days.

(21) Appl. No.: 10/199,861

(22) Filed: Jul. 19, 2002

(65) Prior Publication Data

US 2003/0032583 A1 Feb. 13, 2003

Related U.S. Application Data

(60) Provisional application No. 60/308,885, filed on Jul. 31, 2001.

(51) Int. Cl.$^7$ ............................................... A61K 38/00
(52) U.S. Cl. .......................................................... 514/2
(58) Field of Search ............................................. 514/2

(56) References Cited

U.S. PATENT DOCUMENTS

| | | | | |
|---|---|---|---|---|
| 5,231,085 A | * | 7/1993 | Alexander et al. | ............. 514/44 |
| 5,612,060 A | | 3/1997 | Alexander | |
| 5,733,884 A | | 3/1998 | Barbul et al. | |
| 5,736,178 A | * | 4/1998 | Cook et al. | .................. 426/93 |
| 5,849,335 A | * | 12/1998 | Ballevre et al. | ............ 424/535 |

FOREIGN PATENT DOCUMENTS

| | | |
|---|---|---|
| EP | 0 855 181 | 7/1998 |
| WO | WO 99/49741 | 10/1999 |

OTHER PUBLICATIONS

Brown. Nutricomp Immune. http://tools.search.yahoo.com/language/translation/translatedPage.php?tt=url&text=http%3a//www.provista–online.de/seiten/pdarst__pabc/BRA–008.htm&lp=de__en.*
Boza et al. Nutrition. Plasma glutamine response to enteral administration of glutamine in human volunteers (free glutamine versus protein–bound glutamine). Nov.–Dec. 2000; 16(11–12): 1037–42.*

* cited by examiner

Primary Examiner—Christopher R. Tate
Assistant Examiner—Maury Audet
(74) Attorney, Agent, or Firm—Gary M. Lobel; John W. Kung

(57) ABSTRACT

The present invention is an immunostimulatory composition that bolsters or enhances the immune system in injured, diseased, traumatized or otherwise critically ill patients whose own immune system has been compromised thereby. The ready to feed, liquid formulation comprises glutamine which is stabilized and highly bioavailable in the form of a peptide bound glutamine. Other components comprise the free amino acids such as arginine, a nucleobase such as RNA and omega-3 and omega-6-polyunsaturated fatty acids.

11 Claims, No Drawings

GLUTAMINE RICH DIETARY COMPOSITION

This application claims the benefit of U.S. Provisional No. 60/308,885 filed Jul. 31, 2001.

The present invention relates to enteral nutritional formulations. More particularly, the present invention comprises enhanced nutritional formulas which not only supply the necessary nutritional vitamins, minerals, proteins and carbohydrates but which also bolster the patient immune system as well.

Critically ill or injured tube-fed patients have unique nutritional needs that are not met by standard enteral formulas. Surgery, trauma, burns, sepsis and other illnesses or injuries that induce a hypermetabolic response (HMR) alter the patients' nutritional requirements. The HMR alters substrate metabolism, and increases protein and caloric requirements. Non-essential amino acids such as glutamine and arginine become conditionally essential as a result of this altered metabolic state. Because the gut may be compromised as a result of severe illness or injury, a hydrolyzed protein or "peptide" formula may be better absorbed and utilized than an intact protein formula. For patients suffering from the HMR providing an elemental or semi-elemental diet is highly desirable.

In recent years, attention has been focused on identifying the biochemicals or nutrients that are missing from commercially available parenteral nutritional products and enteral diets. It has been demonstrated that the addition of nucleic acids (RNA) to defined formula diets fed to animals resulted in improved host defense mechanisms. It has also been shown that when arginine is fed at levels exceeding the body's need for protein synthesis, host defense mechanisms are enhanced. This is evidenced by the increased blastogenesis of lymphocytes in response to mitogens in animals and human; reduced tumor appearance and incidence; and increased receptivity of cells to lymphokines.

It has also been observed that omega-6 fatty acids (polyunsaturated vegetable oils typically found as the source of lipids in nutritional products) enter the body's metabolic pathways where they serve as precursors to the family of prostaglandins associated with inflammation and suppression of host defense mechanisms. Omega-3 fatty acids (typically found in fish oils) administered to man or animals either parenterally or enterally, enter the biosynthetic pathways and are preferentially converted to the family of prostaglandins that have not been found to be either inflammatory in nature nor immunosuppressive.

U.S. Pat. No. 5,612,060 to Alexander teaches and claims an improved immunomodulatory therapy for the enhancement of depressed host defense mechanisms. The therapy comprises the administration to the patient of a composition comprising an amino acid such as arginine, ornithin, their salts and mixtures thereof, a nucleotide such as RNA and fish oil as a source of omega-3 fatty acids. The immunomodulatory diet is administered in conjunction with a donor specific transfusion and cyclosporine.

U.S. Pat. No. 5,733,884 to Barbul et. al. discloses a nutritional composition that promotes wound healing consisting of a protein source comprising arginine and proline components in an amount of at least 2.0% of the protein amino acid content, a lipid source selected from the group consisting of medium and long chain triglycerides, a carbohydrate source such as corn starch, hydrolyzed starch, maltose, sucrose and mixtures thereof, omega-3 fatty acids, vitamins and minerals. The compositions are administered to minimize the threat of complications after surgery.

U.S. Pat. No. 5,231,085 to Alexander discloses compositions and methods for the enhancement of host defense mechanisms which initiate an immunostimulatory response. The compositions consist of an intermediate of polyamine synthesis such as arginine, arginine precursors, ornithine and the like. Other components consist of a nucleobase source, omega-3-polyunsaturated fatty acids and omega-6-polyunsaturated fatty acids. The compositions are asserted to enhance the recovery of a deficient or suppressed immune system in humans.

EP 0 855 181 to Konig discloses a nutritional formulation for immune-modulation comprising the free forms of several amino acids, namely, glycine, L-alanine and/or L-serine and their physiologically acceptable salts. Other components of the formulation consist of omega-6-polyunsaturated fatty acids, a second amino acid source, L-arginine and a nucleobase source such as RNA.

U.S. Pat. No. 5,849,335 to Balleure et. al. teaches a nutritional protein composition that is rich in glutamine. Carbohydrates, lipids, vitamins and minerals are also added to the formulation which is particularly useful in the recovery of stressed muscles after exercise, as a nutritional aid for ill or injured patients or as a post-surgical treatment therapy.

PCT/EP99/01274 to Boza et. al. discloses a nutritional composition consisting of whey protein or hydrolyzed whey protein together with a glutamine source utilized in order to increase plasma glutamine levels. The nutritional composition may also further comprise a carbohydrate source selected from the group consisting of maltodextrin, corn starch, lactose and the like. A lipid source may comprise sunflower oil, safflower oil, palm oil, soy oil, medium and long chain triglycerides and mixtures thereof. The composition is disclosed as being especially suitable for athletes after strenuous exercise and pre-term babies.

Glutamine is considered to be a non-essential amino acid. However, glutamine performs many functions in which its demand may be increased. It is a precursor of the synthesis of nucleotides and it is also an activator of protein synthesis while at the same time it inhibits protein degradation. It is an activator of glycogen synthesis and serves as a metabolic substrate for rapidly replicating cells. Glutamine is an energy source for the enterocyte which is important for maintaining the integrity and the function of the intestinal barrier, and the consumption thereof may be increased under conditions of stress.

It has been shown that nutritional adjunctive therapy given to patients either by mouth (enteral) or by vein (parenteral) is efficacious in reversing catabolism and stimulating anabolism. This improvement in the metabolic state of the patient is believed to be highly helpful in the healing process. However, it has also been observed that patients receiving chemically defined parenteral and enteral nutritional regimens often have compromised host defense mechanisms. This compromise of the immune system, even when the metabolic system is improving, may lead to increased morbidity and mortality as a result of sepsis and multiple organ failure. Accordingly, the immunomodulatory effects of glutamine is highly beneficial for injured or critically ill patients.

Although the immunomodulatory effects of glutamine and its ability to enhance the immune systems are known, it has been difficult to provide it in a stabilized form since glutamine is readily converted to glutamate in liquid formulations. Glutamate does not provide the same immune-enhancing effects. Additionally, a ready to use liquid formulation must be shelf-stable and has proper consistency and viscosity such that it can be administered to a patient by conventional means, e.g., drinking or tube-feeding. Moreover, glutamine is not readily bioavailable and metabolized in most protein forms incorporated in the formulations known in the art and commercially available since most of the protein is intact protein which is not easily digested and absorbed.

There are commercially available elemental diet compositions that contain a high level of glutamine. However, these and the other prior art compositions are formulated as dry powders, and when these powdered forms are mixed with water to create to prepare the final product, the glutamine in the composition tends to convert to glutamate. There remains a need for a glutamine-stable, ready to feed immunomodulatory liquid composition.

SUMMARY OF THE INVENTION

The present invention is a nutritional composition that bolsters or enhances the immune system, especially for injured, diseased, traumatized or otherwise critically ill patients whose own immune system has been compromised. The ready to feed, liquid formulation has glutamine which is stabilized and highly bioavailable in the peptide bound form. The present invention provides a stable liquid glutamine-rich nutritional composition containing a wheat protein hydrolysate, caseinate and polyunsaturated fatty acids. Other suitable components for the composition include the free amino acids arginine, other amino acids and their salts, a nucleobase, e.g., RNA, a glyceride, and polyunsaturated fatty acids, e.g., omega-3 and omega-6-polyunsaturated fatty acids. The present invention further provides a method for administering glutamine to a subject. The method has the step of providing a formulation containing a wheat protein hydrolysate, caseinate and polyunsaturated fatty acids. The invention also provides a method for stabilizing a glutamine-rich nutritional composition, which method has the steps of providing a composition comprising a wheat protein hydrolysate, and adding caseinate in said composition.

The compositions of the invention are particularly suitable for administration to the gastro-intestinal tract via feeding tube, but may also be used for oral ingestion.

DETAILED DESCRIPTION OF THE INVENTION

The present invention provides an improved immunostimulatory dietary formulation which is a ready-to-use liquid formulation containing a high level of glutamine. The glutamine is present in a free peptide bound form, especially di- and/or tri-peptide, and is highly bioavailable and readily absorbed by the gut and subsequently metabolized. Particularly suitable di- and tri-peptides for the present invention are L-alanyl-glutamine, L-glycyl-glutamine and mixtures thereof. Useful sources of these peptides are hydrolyzed wheat protein and caseinate.

The formulation can also have other dietary/nutritional ingredients including a fiber source, which is selected from soluble and insoluble fibers and mixtures thereof, that provides additional health benefits for the patient's colon by promoting the production of short chain fatty acids and normalizing the water content of the patient's stools. The present formulation is a liquid composition that is phase stable, i.e., the formulation does not phase separate.

The present formulation contains a glutamine-rich first amino acid source, preferably a wheat protein hydrolysate, and a second amino acid source, preferably caseinate, which stabilizes the first amino acid source. Preferably, the primary source of amino acids in the present formulation is the first amino acid source. The glutamine-rich amino acid source provides peptide bound glutamine, especially di- and/or tri-peptides. Preferably, the first amino acid source in the formulation makes up between about 65 wt % and about 85 wt %, more preferably between about 68 wt % and about 80 wt %, most preferably between about 70 wt % and about 75 wt %, of the total weight of the two amino acid sources. In addition, as a preferred embodiment, the two amino acid sources make up between about 1 wt % and about 20 wt %, preferably between about 3 wt % and about 8 wt %, more preferably between about 5 wt % and about 7 wt %, of the total weight of the formulation. Suitable wheat protein hydrolysates for the present invention are highly hydrolyzed. At least 50 w/w % of the wheat protein hydrolysate has a molecular weight of less than 1,000 Dalton, preferably less than 500 Dalton. Preferably, more than 80 wt % of the wheat protein hydrolysate has a molecular weight of less than 1,000 Dalton and the wheat protein hydrolysate has less than 1 wt % of protein having a molecular weight higher than 10,000 Dalton. It has been found that wheat protein hydrolysates contain bound glutamine, unlike soy protein hydrolysates which contain free glutamine. The term glutamine-rich as used herein indicates a protein source containing more than 20% of its amino acids as glutamine.

As indicated above, caseinate is preferred as the second amino acid source. It has been found that caseinate is not only a good source of the bound glutamine, but also enhances the phase stability of the liquid formulation. Suitable caseinate for the present invention include sodium caseinate and calcium caseinate, which are widely available from commercial sources. Preferably, the caseinate is not a significantly hydrolyzed caseinate. As a preferred embodiment of the present invention, the suitable caseinate is sodium caseinate. In contrast to the wheat protein hydrolysate, the non-hydrolyzed caseinate is composed largely of proteins with molecular weights in excess of 10,000 Dalton. Preferably, the second amino acid source makes up between about 1 wt % and about 3 wt %, more preferably between about 1.5 wt % and about 2 wt %, most preferably between about 1.7 wt % and about 1.9 wt %, of the total weight of the formulation.

Exemplary immunostimulatory formulations of the present invention have a glutamine-rich, di- or tripeptide; a stabilizing protein source; soluble and insoluble fiber; a compound associated with the synthesis of polyamines; a nucleobases source; and polyunsaturated fatty acids, e.g., omega-3-polyunsaturated fatty acids and omega-6-polyunsaturated fatty acids. Suitable sources of the fiber include cellulose and its derivatives, gluten, soy, partially hydrolyzed guar, and mixtures thereof. The term "a compound associated with the synthesis of polyamines" as used herein is intended to include, but not limited to, arginine, arginine precursors, ornithine and the like, in their free amino acid or salt forms. Of the compounds associated with the synthesis of polyamines, free arginine is preferred. Preferably, the compound associated with the synthesis of polyamines makes up between about 0.5 wt % and about 3.5 wt %, more preferably between about 1 wt % and about 2 wt %, most preferably between about 1.4 wt % and about 1.6 wt %, of the total weight of the formulation.

Nucleobase sources suitable for use in the compositions of the present invention include natural nucleobases, nucleosides, nucleotides, RNA, DNA, equivalents thereof and/or mixtures comprising one or more of these compounds. Natural nucleobases include the purines, i.e., adenine and guanine, as well as the pyrimidines, i.e., cytosine, thymine and uracil. Natural nucleosides also include the ribose nucleosides adenosine, guanosine, uridine and cytidine and the deoxyribose nucleosides deoxyadenosine, deoxyguanosine, deoxythymidine and deoxycytidine. Natural nucleotides include the phosphate esters of natural nucleosides, such as the monophosphates adenylate (AMP), guanylate (GMP), uridylate (UMP), cytidylate (CMP), deoxythymidylate (dTMP) deoxycytidylate (dCMP), as well as the diphosphates and triphosphates of natural nucleosides such as ADP and ATP. Preferably, the nucleobase makes up between about 0.1 wt % and about 0.3 wt %, more preferably between about 0.15 wt % and about 0.2 wt %, most preferably between about 0.17 wt % and about 0.18 wt %, of the total weight of the formulation.

Polyunsaturated fatty acids are well known in the art as those having two or more double bonds per molecule and are available from a variety of plant, animal and synthetic sources. Preferred polyunsaturated fatty acids (PUFA) for use according to this invention include the omega-3 PUFA and omega-6 PUFA and mixtures thereof. Examples of omega-3 PUFA particularly appropriate for use in the compositions of the invention include eicosapentaenoic acid (EPA) and docosahexaenoic acid (DHA). The omega-3 and the omega-6 PUFA useful in this invention may be in the free acid form or in a form suitable for the physiological supply of omega-3 or omega-6 PUFA, such as the triglyceride form. Suitable sources for such omega-3 PUFA include linseed oil, canola oil and fish oils such as menhaden oil, salmon oil, mackeral oil, cod oil, herring oil, sardine oil, capelin oil and blends thereof. The amount of omega-3 PUFA to be administered will inter alia depend on the type of treatment, the subject to be treated and the like. Thus, where the subject to be treated is an adult person a satisfactory immunostimulatory response is, in general, obtained with compositions of the invention formulated to allow a daily dosage of from about 0.1 to 20 grams, preferably from 0.1 to 15 grams, most preferably from 0.15 to 10.0 grams of omega-3 fatty acids.

Examples of omega-6 PUFA particularly appropriate for use according to the invention include linoleic acid and arachidonic acid (ETA), linoleic acid being most preferred. Examples of suitable omega-6 PUFA sources include vegetable oils. Preferred are omega-6 PUFA sources having a high linoleic acid content such as safflower oil, sunflower oil, soya oil, cotton oil and corn oil. The amount of omega-6 PUFA to be supplied will inter alia depend on the type of treatment, the subject to be treated and the like. Typically, the compositions of the invention will provide for a daily dosage of from 0.1 to 20 grams, preferably 0.15 to 15 grams, most preferably 0.5 to 10 grams of omega-6 PUFA.

The formulation of the present invention preferably has a dispersion enhancing agent. Suitable dispersion enhancing agents include glycerides, e.g., mono- and di-glycerides and mixtures thereof. The dispersion enhancing agent is added between about 0.05 wt % and about 0.5 wt %, preferably between about 0.1 wt % and about 0.3 wt %, more preferably between about 0.15 wt % and about 0.25 wt %, most preferably between about 0.18 wt % and about 0.22 wt %, based on the total weight of the formulation.

The formulation may additionally contain vitamins and minerals. Examples of suitable vitamins include vitamin A, vitamin D, vitamin E, vitamin K, vitamin C, folic acid, thiamine, riboflavin, vitamin $B_6$, vitamin $B_{12}$, niacin, biotin and panthotenic acid in their pharmaceutically acceptable forms. Examples of mineral elements that are suitable for incorporation in the formulation of the invention include sodium, potassium, calcium, phosphorus, magnesium, manganese, copper, zinc, iron, selenium, chromium and molybdenum in pharmaceutically acceptable form. In particular, the formulation has beta-carotene (vitamin A), vitamin E, vitamin C, thiamine, vitamin $B_{12}$, choline, selenium and zinc in pharmaceutically acceptable form.

Typically, the amounts of the above-indicated components in the formulation of the present invention suitable to meet the daily requirements of a patient suffering from depressed host defense mechanisms will comprise from 3 to 40 grams of arginine, or a physiologically equivalent amount of another compound associated with the synthesis of polyamines or of a mixture of such compounds in association with from about 0.1 to 4.0 g of nucleobase source, of 0.1 to 20 g omega-3 fatty acids and from 0.1 to 20 gm, omega-6 fatty acids. Such unit daily amount will conveniently provide an energy supply of from 750 to 3500 kcal/day.

The immunostimulatory compositions of this invention are suitable for use in patients who suffer from depressed host defense mechanisms, such as patients who suffer from depressed host defense mechanisms as a result of post-surgical trauma, cancer, chemotherapy/radiation therapy, sepsis, trauma, bums, immunosuppressive drug therapy, malnutrition, transfusion-induced immunosuppression and the like. It has indeed been observed that the body, when under severe stress, cannot readily mobilize the nutrients necessary to secure a normal immune function. The administration of the compositions of the invention allows to maintain, restore and enhance the immune function where desired. The immune system reacts surprisingly quickly and favorably to the administration of these compositions. Such compositions may accordingly be employed to enhance a depressed host defense mechanism, to restore a normal immune function in a human with a deficient immune response, to enhance the development of the immune system in a developing human, to enhance a senescent immune system of a human and the like. The invention accordingly also provides the composition of the invention for use in a method of maintaining or stimulating the immune system of a patient, in need of such treatment.

The following examples are provided to more specifically define and set forth the compositions useful as immunostimulatory dietary formula. They are for illustrative purposes only, and it is recognized that changes and alternatives may be made thereto that are not contemplated herein. It is to be understood then that to the extent any such changes or alternatives do not materially alter the makeup or function of these compositions, any such changes are deemed to fall within the spirit and scope of the invention as defined by the claims that follow.

EXAMPLE 1

An immunostimulatory dietary formula of the present invention is prepared from the following components in their respective amounts. The percentage amounts are in terms of weight percent.

| Component | Percent |
|---|---|
| Deionized water | 71.7 |
| Maltodextrin[1] | 12.7 |
| Hydrolyzed wheat protein[2] | 4.6 |
| Sodium caseinate | 1.8 |
| Mono and diglycerides[3] | 0.2 |
| Vegetable oil[4] | 2.2 |

-continued

| Component | Percent |
|---|---|
| Menhaden oil[5] | 1.6 |
| Carrageenan[6] | 0.2 |
| Fiber Blend[7] | 0.9 |
| Amino Acid Blend[8] | 2.4 |
| Vitamin/Mineral Blend[9] | 0.7 |
| Citric Acid | 0.4 |
| Potassium Citrate | 0.3 |
| Sodium Phosphates | 0.2 |
| TOTAL | 100.0 |

Note:
[1]Maltrin M-100, Grain Processing Corp., Muscataine, Iowa
[2]WGE80GPA, DMV International, Freser, New York
[3]Atmos 300, Atlas Chemical Co.
[4]A mixture of 79% palm kernal oil and 21% sunflower oil
[5]Refined, unhydrogenated
[6]A mixture of Seaken CM614 and Gelcarin GP379, FMC
[7]A mixture of 58% guar and 42% soy polysaccharides
[8]A blend of lysine acetate, L-leucine, L-threonine, L-histidine, L-tryptophan, L-methionine, and L-valine
[9]A blend of maltodextrin (38.8%), beta carotene-1% (20%), vitamin E acetate-50% (14%), vitamin A palmitate (5.7%), zinc sulfate (4%), ferrous sulfate (4%), biotin-1% (2.6%), calcium pantothenate (2.4%), niacinamide (1.8%), vitamin K (1.7%), copper gluconate (1.1%), vitamin B12 (0.9%), folic acid-10% (0.8%), vitamin D3 (0.5%), manganese sulfate (0.5%), pyridoxine HCl (0.4%), potassium iodide (0.3%), thiamine HCl (0.3%), riboflavin (0.2%), chromic acetate (0.04%), sodium molybdate (0.01%), and sodium selenite (0.01%).

The components are mixed together and blended using standard equipment. This level of caseinate was found to give an excellent emulsion while still maximizing the amount of glutamine supplied by the formula at a particular protein level. The formulation is stable and does not separate.

EXAMPLES 2 and 3

Example 1 is repeated except the levels of hydrolyzed wheat protein are decreased to 4.0% and 3.3% while keeping the total content of the two protein sources. The formulations have more superior emulsion stability, but contain lower amounts of bound glutamine.

COMPARATIVE EXAMPLE

Example 1 is repeated except caseinate is removed from the formulation. When the formulation is stored at room temperature, the formulation separated with two to three days. This example clearly demonstrate that the formulation produced in accordance with the present invention is a stable formulation. The ready to feed, liquid formulation of the present invention, which contains glutamine, is stable and provides stable peptide bound glutamine that is readily bioavailable.

What is claimed is:

1. A stable liquid glutamine-rich nutritional composition comprising a wheat protein hydrolysate, caseinate and polyunsaturated fatty acids, wherein said caseinate is comprised between 1 wt % and 3 wt % based on the total weight of said composition.

2. The nutritional composition of claim 1 wherein said caseinate is sodium caseinate.

3. The nutritional composition of claim 1 wherein said polyunsaturated fatty acids comprise omega-3 fatty acids and omega-6 fatty acids, and comprise between 1 wt % and 7 wt %, based on the total weight of said composition.

4. The nutritional composition of claim 1 wherein said composition further comprises a nucleobase.

5. The nutritional composition of claim 1 wherein said composition further comprises free arginine.

6. The nutritional composition of claim 1 wherein said wheat protein hydrolysate comprises between 65 wt % and 85 wt % of the combined total weight of said wheat protein hydrolysate and said caseinate.

7. The nutritional composition of claim 1 wherein said composition further comprises a glyceride selected from the group consisting of monoglyceride, diglyceride and mixtures thereof.

8. The nutritional composition of claim 4 wherein said nucleobase is RNA and RNA comprises between 0.1 wt % and 0.3 wt %, based on the total weight of the composition.

9. The nutritional composition of claim 5 wherein said arginine comprises between 0.5 wt % and 3.5 wt %, based on the total weight of the composition.

10. A method for providing glutamine to a subject comprising the step of providing a formulation comprising a wheat protein hydrolysate, caseinate and polyunsaturated fatty acids, wherein said caseinate is comprised between 1 wt % and 3 wt % based on the total weight of said formulation.

11. A method for stabilizing a glutamine-rich nutritional composition comprising the steps of providing a composition comprising a wheat protein hydrolysate and polyunsaturated fatty acids and adding between 1 wt % and 3 wt % caseinate to said composition, based on the total weight of said composition.

* * * * *